United States Patent
Kiderman et al.

(10) Patent No.: US 10,743,808 B2
(45) Date of Patent: *Aug. 18, 2020

(54) METHOD AND ASSOCIATED APPARATUS FOR DETECTING MINOR TRAUMATIC BRAIN INJURY

(71) Applicants: Alexander D Kiderman, Pittsburgh, PA (US); James Z Cinberg, South Orange, NJ (US)

(72) Inventors: Alexander D Kiderman, Pittsburgh, PA (US); James Z Cinberg, South Orange, NJ (US)

(73) Assignees: NEURO KINETICS, Pittsburgh, PA (US); James Z Cinberg, South Orange, NJ (US)

( * ) Notice: Subject to any disclaimer, the term of this patent is extended or adjusted under 35 U.S.C. 154(b) by 1542 days.

This patent is subject to a terminal disclaimer.

(21) Appl. No.: 14/284,718

(22) Filed: May 22, 2014

(65) Prior Publication Data
US 2015/0018709 A1 Jan. 15, 2015

Related U.S. Application Data

(63) Continuation of application No. 13/971,111, filed on Aug. 20, 2013, now Pat. No. 8,808,179, which is a (Continued)

(51) Int. Cl.
*A61B 5/00* (2006.01)
*A61B 3/00* (2006.01)
(Continued)

(52) U.S. Cl.
CPC .............. *A61B 5/4064* (2013.01); *A61B 3/00* (2013.01); *A61B 3/02* (2013.01); *A61B 3/113* (2013.01); *A61B 5/1104* (2013.01); *A61B 5/163* (2017.08)

(58) Field of Classification Search
CPC ................ G06Q 50/22; G06F 19/3431; A61K 2300/00; C12Q 1/6883; C12Q 1/6886;
(Continued)

(56) References Cited

U.S. PATENT DOCUMENTS 3,612,642 A 10/1971 Dostal
4,006,974 A 2/1977 Resnick
(Continued)

FOREIGN PATENT DOCUMENTS

JP 11/184621 7/1999

OTHER PUBLICATIONS

Maria Fontanazza, Device Eases Diagnosis of Concussions and Other Cognitive Conditions, http://www.devicelink.com/mddi/archive/05/07/010.html.
(Continued)

*Primary Examiner* — Sanjay Cattungal
(74) *Attorney, Agent, or Firm* — Blynn L. Shideler; Krisanne Shideler; BLK Law Group (57) ABSTRACT

Minor traumatic brain injury is detected by operating (a) an image generator for presenting a visual stimulus having a predetermined movement across a visual field of a subject and (b) a sensor device for monitoring fast eye movement of the subject while the subject views the stimulus. The sensor device generates a signal encoding the subject's eye position. A computer or microprocessor operatively connected to the sensor device is configured for determining a magnitude for the fast eye velocity component.

18 Claims, 2 Drawing Sheets

Related U.S. Application Data continuation of application No. 13/567,670, filed on Aug. 6, 2012, now Pat. No. 8,585,589.

(51) Int. Cl.
   *A61B 5/16* (2006.01)
   *A61B 3/113* (2006.01)
   *A61B 5/11* (2006.01)
   *A61B 3/02* (2006.01)

(58) Field of Classification Search
   CPC ........ A61B 5/4064; A61B 5/163; A61B 3/02; A61B 5/1104; A61B 3/113; A61B 3/00
   USPC ........ 600/407–480, 544–548, 300, 382–384; 351/209–211
   See application file for complete search history.

(56) References Cited

U.S. PATENT DOCUMENTS

| | | |
|---|---|---|
| 4,084,182 A | 4/1978 | Maiman |
| 4,309,608 A | 1/1982 | Adamson |
| 4,320,768 A | 3/1982 | Ledley et al. |
| 4,474,186 A | 10/1984 | Ledley et al. |
| 4,572,199 A | 2/1986 | LaCourse |
| 4,836,219 A | 6/1989 | Hobson et al. |
| 4,852,988 A | 8/1989 | Velez et al. |
| 4,863,259 A | 9/1989 | Schneider et al. |
| 5,070,883 A | 12/1991 | Kasahara |
| 5,098,426 A | 3/1992 | Sklar et al. |
| 5,130,838 A | 7/1992 | Tanaka et al. |
| 5,252,999 A | 10/1993 | Sukigara et al. |
| 5,304,112 A | 4/1994 | Mrklas et al. |
| 5,305,746 A | 4/1994 | Fendrock |
| 5,320,109 A | 6/1994 | Chamoun et al. |
| 5,345,281 A | 9/1994 | Taboada et al. |
| 5,365,941 A | 11/1994 | Yoshimatsu |
| 5,368,041 A | 11/1994 | Shambroom |
| 5,381,804 A | 1/1995 | Shambroom |
| 5,410,376 A | 4/1995 | Cornsweet et al. |
| 5,458,117 A | 10/1995 | Chamoun et al. |
| 5,481,622 A | 1/1996 | Gerhardt |
| 5,491,492 A | 2/1996 | Knapp |
| 5,652,756 A | 7/1997 | Stultz et al. |
| 5,687,020 A | 11/1997 | Park et al. |
| 5,704,369 A | 1/1998 | Scinto |
| 5,714,967 A | 2/1998 | Okamura et al. |
| 5,792,069 A | 8/1998 | Greenwald et al. |
| 5,813,404 A | 9/1998 | Devlin et al. |
| 5,821,521 A | 10/1998 | Bridgelall et al. |
| 5,838,420 A | 11/1998 | MacGregor Donaldson |
| 5,877,732 A | 3/1999 | Ziarati |
| 5,892,566 A | 4/1999 | Bullwinkel |
| 5,942,954 A | 8/1999 | Galiana |
| 5,943,116 A | 8/1999 | Zeimer |
| 5,963,300 A | 10/1999 | Horwitz |
| 5,980,513 A | 11/1999 | Frey et al. |
| 5,983,128 A | 11/1999 | Baudonniere |
| 6,003,991 A | 12/1999 | Virre |
| 6,024,707 A | 2/2000 | Scinto |
| 6,032,064 A | 2/2000 | Devlin et al. |
| 6,032,072 A | 2/2000 | Greenwald et al. |
| 6,033,073 A | 3/2000 | Potapova |
| 6,077,237 A | 6/2000 | Campbell |
| 6,089,716 A | 7/2000 | Lashkari et al. |
| 6,090,051 A | 7/2000 | Marshall |
| 6,099,124 A | 8/2000 | Hadaji |
| 6,113,237 A | 9/2000 | Ober |
| 6,120,461 A | 9/2000 | Smyth |
| 6,162,186 A | 12/2000 | Scinto |
| 6,213,943 B1 | 4/2001 | Abreu |
| 6,231,187 B1 | 5/2001 | Munoz |
| 6,247,813 B1 | 6/2001 | Kim et al. |
| 6,271,915 B1 | 8/2001 | Frey et al. |
| 6,275,718 B1 | 8/2001 | Lempert |
| 6,299,308 B1 | 10/2001 | Veronka et al. |
| 6,367,932 B1 | 4/2002 | Donaldson |
| 6,402,320 B1 | 6/2002 | Borchert |
| 6,456,261 B1 | 9/2002 | Zhang |
| 6,459,446 B1 | 10/2002 | Harman |
| 6,467,905 B1 | 10/2002 | Stahl |
| 6,637,883 B1 | 1/2003 | Tengshe |
| 6,524,581 B1 | 2/2003 | Adamis |
| 6,542,081 B2 | 4/2003 | Torch |
| 6,551,575 B1 | 4/2003 | Greenspan |
| 6,568,808 B2 | 5/2003 | Campin |
| 6,574,352 B1 | 6/2003 | Skolmoski |
| 6,609,523 B1 | 8/2003 | Anthony |
| 6,629,935 B1 | 10/2003 | Miller |
| 6,631,989 B2 | 10/2003 | Odom et al. |
| 6,634,749 B1 | 10/2003 | Morrison et al. |
| 6,652,458 B2 | 11/2003 | Blazey |
| 6,659,611 B2 | 12/2003 | Amir et al. |
| 6,669,341 B2 | 12/2003 | Wirth |
| 6,697,894 B1 | 2/2004 | Mitchell et al. |
| 6,748,275 B2 | 6/2004 | Lattner |
| 6,796,947 B2 | 9/2004 | Watt |
| 6,800,062 B2 | 10/2004 | Epley |
| RE38,668 E | 12/2004 | Edwards |
| 6,943,754 B2 | 9/2005 | Aughey et al. |
| 7,115,099 B2 | 10/2006 | Miller et al. |
| 7,398,119 B2 | 7/2008 | Lambert et al. |
| 7,448,751 B2 | 11/2008 | Kiderman et al. |
| 7,520,614 B2 | 4/2009 | Joos et al. |
| 7,651,224 B2 | 1/2010 | Wood et al. |
| 7,665,845 B2 | 2/2010 | Kiderman et al. |
| 7,819,818 B2 | 10/2010 | Ghajar |
| 7,988,287 B1 | 8/2011 | Butler et al. |
| 8,065,240 B2 | 11/2011 | Jung et al. |
| 8,333,472 B2 | 12/2012 | Kiderman |
| 8,406,859 B2 | 3/2013 | Zuzak et al. |
| 8,568,311 B2 | 10/2013 | LaPlaca et al. |
| 8,585,589 B1 | 11/2013 | Cinberg |
| 8,585,609 B2 | 11/2013 | Kidderman et al. |
| 8,808,179 B1 | 8/2014 | Cinberg |
| 2002/0027779 A1 | 3/2002 | Cassarly |
| 2002/0085174 A1 | 7/2002 | Bolger |
| 2002/0171805 A1 | 11/2002 | Odom et al. |
| 2002/0175880 A1 | 11/2002 | Melville |
| 2003/0028081 A1 | 2/2003 | Blazey |
| 2004/0181168 A1 | 3/2004 | Plant |
| 2005/0004489 A1 | 1/2005 | Sarkela et al. |
| 2005/0024586 A1 | 2/2005 | Teiwes |
| 2005/0216243 A1 | 3/2005 | Graham |
| 2005/0079636 A1 | 4/2005 | White |
| 2005/0099601 A1 | 5/2005 | MacDougall et al. |
| 2005/0101877 A1 | 5/2005 | Miller |
| 2005/0110950 A1 | 5/2005 | Thorpe |
| 2006/0098087 A1 | 5/2006 | Brandt et al. |
| 2006/0235331 A1 | 10/2006 | Kiderman |
| 2007/0132841 A1 | 6/2007 | MacDougall et al. |
| 2008/0273084 A1 | 11/2008 | MacDougall et al. |
| 2008/0278685 A1 | 11/2008 | MacDougall et al. |
| 2009/0118593 A1 | 5/2009 | Jung et al. |
| 2009/0119154 A1 | 5/2009 | Jung et al. |
| 2009/0132275 A1 | 5/2009 | Jung et al. |
| 2009/0307179 A1 | 10/2009 | Colby et al. |
| 2009/0307180 A1 | 10/2009 | Colby et al. |
| 2009/0307181 A1 | 10/2009 | Colby et al. |
| 2009/0299645 A1 | 12/2009 | Colby et al. |
| 2010/0280372 A1 | 11/2010 | Poolman et al. |
| 2011/0086914 A1 | 4/2011 | Bailes |
| 2011/0208060 A1 | 8/2011 | Haase et al. |
| 2011/0229862 A1 | 8/2011 | Parikh |
| 2012/0330178 A1 | 10/2012 | Kraft et al. |
| 2014/0192326 A1 | 7/2014 | Kiderman |

OTHER PUBLICATIONS

Jason S. Babcock, Jeff B. Pelz, Building a lightweight eyetracker, http://www.cis.rit.edu/people/faculty/pelz/publications/ETRA04_babcock_pelz.pdf, 2004.

(56) References Cited

OTHER PUBLICATIONS

D. Zhu et al., Computer Methods and Programs in Biomedicine 59 (1999), pp. 146-157.
Hamish G. MacDougall, Applicants description of Prior Art Systems, Applicants internal memo regarding Prior Art.
Moore et al., A geometric Basis for Measurement of Three-Dimensional Eye Position Using Image Processing, pp. 445-459, Vision Res. vol. 36.
Abstract of Y Chiba, M.D. and N. Furuya. M.D.; Aging and Reference Values of the Parameters in Optokinetic Nystagmus; 1989; Oto-Rhino-Laryngological Society of Japan; p. 1416-23.
Abstract of K. Yamada, K. Kaga, N. Furuya;Computer Analysis of the Optokinetic Pattern Test in Acoustic Tumors, Brain Stem and Cerebellar Lesions;Acta Otolaryngol (Stockh) 1991; Suppl. 48.
Cohen B, Matsuo V, Raphan T.; Quantitative analysis of the velocity characteristics of optokinetic nystagmus and optokinetic after-nystagmus.;J. Physiol. (1977), 270, p. 321-324.
Abstract of Kanayama R;Kato I;Nakamura T;Koike Y;The Fast-phase Velocity of Optokinetic Nystagmus in Central Nervous System Disorders;Nov.-Dec. 1987; 104(5-6):39Informa Healthcare, London.

METHOD AND ASSOCIATED APPARATUS FOR DETECTING MINOR TRAUMATIC BRAIN INJURY

RELATED APPLICATIONS

The present application discloses and claims developments invented by Dr. Alexander D. Kiderman and Dr. James Z. Zinberg and is a continuation of pending U.S. patent application Ser. No. 13/971,111 entitled "Method and Associated Apparatus for Detecting Minor Traumatic Brain Injury" filed Aug. 20, 2013, which is incorporated herein by reference. U.S. patent application Ser. No. 13/971,111 is a continuation of patent application Ser. No. 13/567,670 filed Aug. 6, 2013 entitled "Method and Associated Apparatus for Detecting Minor Traumatic Brain Injury" and which issued as U.S. Pat. No. 8,585,589 which is incorporated herein by reference.

BACKGROUND OF THE INVENTION

1. Field of the Invention

The present invention relates to a method for detecting brain injury. More particularly, this invention relates to a noninvasive and atraumatic method for detecting minor traumatic brain injury. This invention also relates to an associated apparatus.

2. Background Information

It is well known that certain contact sports frequently result in injury to the participants. One kind of potential injury that frequently goes undetected is minor traumatic brain injury. (Major traumatic brain injury can hardly fail to be detected even upon cursory inspection.) As minor traumatic brain injury heretofore has been undetectable, the injured sports participant is usually sent back into the fray without treatment of any sort. The injury may be then compounded by further head trauma from forceful engagements ensuing on the field or in the arena.

Minor traumatic brain injury may also be sustained during military conflict. Again, owing to an inability to detect the injury, the injured combatants are returned to the front lines, with the possibility of additional injury to the brain, as well as other organs.

The resulting costs to society are obvious. Multiple minor traumatic brain injuries can give rise to permanent dysfunction and also major injury and the necessity for extensive treatment expenses.

OBJECTS OF THE INVENTION

It is an object of the present invention to provide a method and/or an apparatus for facilitating, if not enabling, the detection of minor traumatic brain injury.

It is another, more particular, object of the present invention to provide such a method and/or apparatus for facilitating, if not enabling, on site detection of minor traumatic brain injury.

It is a further particular object of the present invention to provide such a method and/or an apparatus, which permits a test to be done quickly and which is easy to use.

It is a related object of the present invention to provide such a method and/or an apparatus which does not require the services of trained medical personnel.

These and other objects of the present invention will be apparent from the drawings and descriptions herein. It is to be noted that any single embodiment of the invention may not achieve all of the objects of the invention, but that every object is attained by at least one embodiment.

SUMMARY OF THE INVENTION

A method for detecting minor traumatic brain injury comprises, in accordance with the present invention, presenting to a subject a visual stimulus having a predetermined direction and speed of movement across the visual field of the subject and monitoring the subject's eye movement while the subject views the stimulus, where the eye movement includes a slow eye velocity component and a fast eye velocity component. The slow eye velocity component is responsive or corresponds to the predetermined movement of the visual stimulus, while the fast eye velocity component is typically an involuntary movement in an opposite direction (e.g., retrograde). The monitoring of eye movement includes detecting the fast eye velocity component. Detecting the fast eye component entails sensing the amount of movement of the eye as a function of time. The method further comprises determining a magnitude for a parameter of the detected fast eye velocity component and comparing the determined magnitude with a predetermined numerical value to determine whether the subject has incurred minor traumatic brain injury.

It is contemplated that the method of the present invention is mainly performed automatically. Thus, the monitoring of eye movement may include or be done by a sensor device such as a camera. A digital computer may be operatively connected to the camera, so that the monitoring of eye movement includes operating the digital computer, for instance, to carry out a pattern recognition process and/or a filtering process to identify the fast eye velocity movement.

Preferably, the parameter of fast eye movement is a velocity or speed. In that case, the monitoring of eye movement includes measuring an amplitude or angular distance of a fast eye velocity movement and dividing the measured or angular distance by the duration of the fast eye movement. Thus, the units of the magnitude may be degrees per unit time.

Typically, the stimulus is a striped pattern, specifically, alternating dark and bright vertical bands that move to the right or left. When the stimulus motion is to the right, the fast eye movement is typically to the left and vice versa. What happens generally is that subject fastens his or her focus on the center of the visual field and counts the stripes as they go by. The eye voluntarily registers the bands at a speed consistent with movement across the visual field and involuntarily backtracks in a fast eye movement in the opposite direction, and registers the next band to follow in a slow eye velocity movement. This pattern of alternating fast and slow movements may continue indefinitely, as long as the stimulus is passing across the display screen. The degree or amount that the eye travels during the fast and slow eye movements however differs although the velocity of the stimulus does not.

A plot of eye position/movement may be plotted along the ordinate of a graph, with the abscissa representing time or duration of the stimulus. The resulting plot takes the form of a saw tooth curve, with shallow line segments corresponding to slow eye movement and intercalated steep line segments corresponding to fast eye movements. The slopes of the line segments increase as the eye movement velocity increases. Typically, the saw tooth is irregular with teeth of varying heights, owing to variation in the amplitudes or angular distances traversed by the subject's eye as fast and slow eye movements during a stimulus presentation.

During one stimulus viewing, multiple comparisons of the measured parameter, magnitude of fast eye velocity per amount of eye movement, are made with respect to predetermined numerical values—which are standards or reference thresholds for fast eye movement for degree of eye movement. One measures the fast eye movement velocity for each successive fast eye movement and compares the measured velocity associated with distance traveled each time with the predetermined numerical reference value or threshold. Alternatively, one might select the largest or peak value of eye velocity for each of plurality of ranges of fast eye movement amplitudes (e.g., short, medium, and long) and compare each peak value with a respective predetermined numerical threshold. In each of these cases, the diagnosis of potential brain trauma could depend on the percentage of comparisons where the measured eye velocity falls below a reference or threshold value.

It is possible to use the method and apparatus of the present invention to monitor brain health or integrity using a parameter of eye movement versus eye velocity with analysis of the degree of uniformity among the amplitudes or angular distances of the fast eye movements. Greater uniformity might indicate a potential injury. Conversely, a substantial variation in the amplitudes would indicate an undamaged or healthy brain.

Alternatively, one might construct a graph with the abscissa or x-axis, for example, as the amplitude or degree of eye movement and the ordinate or y-axis the velocity for that movement. (Generally, fast eye movement velocity varies as a function of amplitude or distance—the greater the angular distance through which the eye moves, the more velocity the eye can build up during its transit of that angular distance.) If fast eye velocity falls below 2 standard deviations of norms for any degree of movement, that can be taken as an indicator of potential brain trauma.

Preferably, the multiple amplitudes of fast eye movement are collected by generic digital processing circuits of a microprocessor that are configured through software to analyze each single response, each "triangle" of the saw tooth eye-movement graph of amount of eye position moved vs. time required for the movement, to thereby identify the distances traveled per time elapsed for that travel during the fast phase. The microprocessor may be configured to execute a filter set to screen out eye movement velocities that are too slow to be a fast eye velocity and to screen out eye movement amplitudes of an inappropriate length for a fast eye velocity movement.

Where the parameter of fast eye movement velocity or speed, per amount of eye movement, is used for brain trauma diagnosis, the magnitude of the velocity may be determined by operating the digital computer or microprocessor to carry out an arithmetic calculation—a velocity calculation. As mentioned above, a measured amplitude or angular distance of fast eye movement is divided by the time or duration of the fast eye movement. Again, multiple velocity magnitudes are computed for a single transit of the stimulus across the display screen, one for each fast eye movement.

Magnitudes of fast eye movement velocity vary given that the eye may travel a different length/distance in each eye movement. Velocity varies with the distance traveled in degrees. Also, velocity varies as between a healthy person and a brain injured patient, for the same distance of eye travel. One would have a "normogram" of peak velocities for each distance/amount of eye movement and determine whether a test subject's peak velocities were within 2 standard deviations of the norms. If test subject's peak velocities fall below the norms, that is an indication of brain stem dysfunction.

Where the sensor device and the computer or microprocessor are housed in a casing, the casing may be provided with a display, and the presenting of the stimulus includes operating the computer or microprocessor to provide the stimulus as a moving image on the display.

The casing may take the form of a head mounted device, such as glasses or goggles, in which case the method further comprises removably attaching the casing to a head of the subject prior to the presenting of the stimulus.

The comparing of a measured eye-movement magnitude with a predetermined numerical threshold value may be accomplished automatically via the computer or microprocessor. In an alternative arrangement, the determining of the eye velocity magnitude includes transmitting eye movement data over a computer network and receiving a computed eye movement velocity in return over the computer network. The comparison of a computed eye movement magnitude with a predetermined numerical value may also be performed at a remote location by another computer. In that event, the result of the comparison may be transmitted back to the on site digital computer or microprocessor, either alone or together with a computed magnitude of the fast eye velocity parameter.

Preferably, however, both the determination of a fast eye movement magnitude angular speed per angular distance traveled) and the comparison thereof with a predetermined numerical value or threshold are automatically performed through the operation of a programmed electronic device on site. This ensures that an evaluation may be made at any time and any place, regardless of access to a wireless or other network. An apparatus for detecting minor traumatic brain injury comprises, in accordance with the present invention, (a) an image generator for presenting a visual stimulus having a predetermined movement across the visual field of a subject and (b) a sensor device for monitoring movement of an eye of the subject while the subject views the stimulus. Again, the eye movement includes a slow eye velocity component and a fast eye velocity component, where the slow eye velocity component is responsive to the predetermined movement of the visual stimulus and the fast eye velocity component is typically counter to the direction of movement of the stimulus. The sensor device generates a signal encoding eyeball position. The apparatus further includes a computer or microprocessor operatively connected to the sensor device, the computer or microprocessor being configured for determining a magnitude for the fast eye velocity component. Typically, the magnitude is an angular speed, in degrees per second. The calculation for the magnitude is the distance traveled divided by time elapsed during that travel beginning from initiation to end of eye movement, for each different amount/amplitude of eye movement. Alternatively, a measure of the homogeneity or lack thereof of distribution of velocities/amplitude across multiple fast eye movements will distinguish between normal and brain injury.

Pursuant to another feature of the present invention, the computer or microprocessor is further configured to compare the determined fast eye movement magnitude with a predetermined numerical value to determine whether the subject has incurred minor traumatic brain injury.

In accordance with an additional feature of the present invention, where the sensor device is a camera, the computer or microprocessor is configured for executing a pattern recognition process and a filtering process to identify the fast eye velocity movement. The camera may be an optical camera and/or an infrared camera.

Pursuant to a further feature of the present invention, the sensor device and the computer or microprocessor are housed in (i.e., attached to) a casing, and the casing is provided with a display. In that event, the computer or microprocessor is operatively connected to the display for operating the display to provide the stimulus as a moving image on the display. The casing may be provided with an input capability, such as a keyboard implemented either via mechanical keys or a touch screen on the display. The input device enables the user to vary the stimulus, for instance, the width and/or contrast and/or speed of movement of vertical bands on the display. The display functions in part as a graphical user interface, providing feedback and options to the user, which the user selects via the keyboard or other input functionality.

Preferably, the casing has a hand-holdable configuration and size. The casing may be a notebook sized device or a frame such as eyeglasses or goggles mountable to the head of the subject over the subject's eyes. In that case, a headband or cap or other coupling element is provided for removably attaching the casing to a head of the subject.

In accordance with a supplemental feature of the present invention, the computer or microprocessor is configured for transmitting eye movement data over a computer network and receiving a computed eye movement velocity or diagnostic result in return over the computer network.

A method and/or an apparatus in accordance with the present invention facilitates, if not enables, the detection of minor traumatic brain injury. A test or measurement may be performed on location, thereby enabling an informed decision as to whether a potentially injured sports player or soldier is in fact brain injured and should be at least temporarily withdrawn from continued participation in the physical conflict. A method and/or apparatus in accordance with the present invention is easy and quick to use. The invention may be used without requiring the services of trained medical personnel.

These and other advantages of the present invention will be clarified in the description of the preferred embodiments taken together with the attached drawings in which like reference numerals represent like elements throughout.

BRIEF DESCRIPTION OF THE DRAWINGS

Other objects and advantages appear in the following description and claims. The enclosed drawings illustrate some practical embodiments of the present invention, without intending to limit the scope of the invention or the included claims.

DESCRIPTION OF THE PREFERRED EMBODIMENTS

Figure 1:
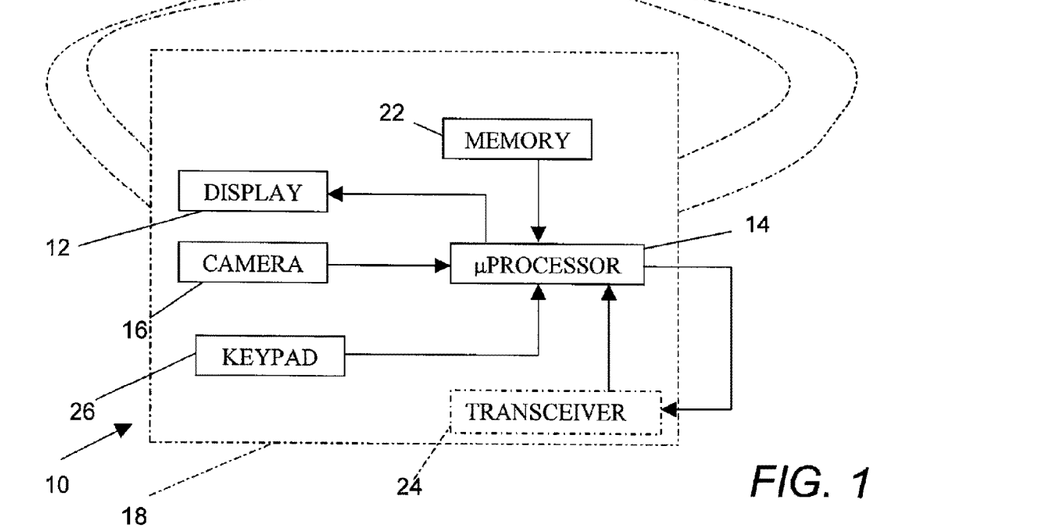
FIG. 1 is a block diagram of a device in accordance with the present invention for detecting potential minor traumatic brain injury.

As depicted in FIG. 1, an apparatus 10 for detecting minor traumatic brain injury comprises a display 12 for presenting a visual stimulus having a predetermined movement across a visual field of a subject. Display 12 is controlled by a microprocessor or digital computer 14, which functions in part, together with the display, as an image generator. The visual stimulus can take any form that is perceptible by a subject and that can move across the display screen. Typically, the visual stimulus takes the form of a series of vertically oriented bars or stripes that move laterally across the display screen, i.e., to the right or the left. Alternatively, the visual stimulus might take the form of a spot or icon or a series of spots or icons, or other graphic representations.

Apparatus 10 further comprises a sensor device 16 for monitoring movement of an eye of the subject while the subject views the stimulus on display 12. Sensor device 16 typically takes the form of an optical or infrared camera. Camera 16 and display 12 are mounted to a frame 18, which may be a casing of a handheld or hand-holdable electronic device such as a notebook computer. In that event, camera 16 is disposed on the same side of the frame or casing 18 as display 12.

Alternatively, frame or casing 18 may be goggles or an eyeglass frame with a coupling or mounting element 20 such as eyeglass arms or a strap or band for removably attaching the eyeglasses to the head of an individual subject. Products such as eyeglasses with incorporated computers and visual displays on the lenses are known in the art.

The eye movement of a subject attending to the moving visual stimulus on display 12 includes a slow eye velocity component and a fast eye velocity component. Sensor device or camera 16 generates a signal encoding the position of the subject's eye at least during the fast eye velocity component. The slow eye velocity component is responsive to the predetermined movement of the visual stimulus. The speed of the fast eye component, if below a certain threshold, may indicate abnormal brain function possibly occasioned by minor traumatic brain injury.

Computer or microprocessor 14 is operatively connected to sensor device or camera 16, the computer or microprocessor being configured for determining a magnitude for a parameter of the fast eye velocity component. The term "magnitude" is used herein to denote a numerical value, positive or negative, characteristic of fast eye movement and used for comparison with another numerical value, namely, a reference value or threshold that is experimentally determined to be indicative of minor traumatic brain injury. A calculated fast eye movement magnitude is derived from detected fast eye movement and may be of any eye movement parameter or mathematical relationship that is determined to be indicative of brain injury.

Computer or microprocessor 14 may also be configured or programmed for comparing the determined eye velocity magnitude with a predetermined threshold stored in a memory 22, to thereby obtain an automated diagnosis of potential minor traumatic brain injury. Alternatively, the computation of fast eye velocity magnitude and the diagnostic comparison with a threshold eye velocity magnitude may be performed by a remote computer (not illustrated) with which computer or microprocessor 14 communicates via a transceiver unit 24, for instance, a dedicated hard-wired communications link or a wireless communications link connecting to the Internet or a private computer network.

The comparison of the measured velocity magnitude with a predetermined numerical value—which is a standard or reference threshold—may occur multiple times during one stimulus viewing. It is possible, for instance, to measure the fast eye movement velocity for each successive fast eye movement and compare the measured velocity each time with the predetermined numerical reference value or threshold.

Alternatively, instead of a single numerical threshold value, one might use a plurality of numerical threshold values each assigned to a particular band of eye movement amplitudes. Each measured fast eye movement velocity is then compared with a threshold value that depends is selected in accordance with the amplitude of the respective fast eye movement. Generally, small amplitudes will have smaller eye speed thresholds or reference values.

An alternative measured parameter may be normalized eye movement velocity, for instance, the velocity of a fast eye movement divided by the distance traveled during that fast eye movement.

In another alternative approach, one might select the largest or peak value of eye velocity for each of plurality of ranges of fast eye movement amplitudes (e.g., short, medium, and long) and compare each peak value with a predetermined numerical threshold allotted to the respective amplitude range. When multiple comparisons are made for testing a single subject, the diagnosis of potential brain trauma could depend on the percentage of positives, i.e., comparisons where the measured eye velocity (whether individual or peak) falls below a reference or threshold value.

Frame or casing 18 may be provided with an input capability, such as a keyboard 26 implemented either via mechanical keys or a touch screen on the display 12. In that case, display 12 functions in part as a graphical user interface, providing feedback and options to the user, which the user selects via keyboard 26 or other input functionality. Options may include characteristics of the stimulus such as size, shape, contrast, and direction and speed of movement. Other options may include the kind of parameter that is to be measured and compared with a threshold. As indicated above, possible parameters include fast eye movement velocity, normalized fast eye movement velocity, and distribution of fast eye movement amplitudes.

Where fast eye movement velocity is the selected parameter, additional options include the number and types of comparisons that are undertaken. Comparison with a threshold might be undertaken for each fast eye movement during the course of a stimulus presentation. Alternatively, comparisons might be undertaken for only those fat eye movements where the eye movement amplitude exceeds a preselected value.

Figure 2:
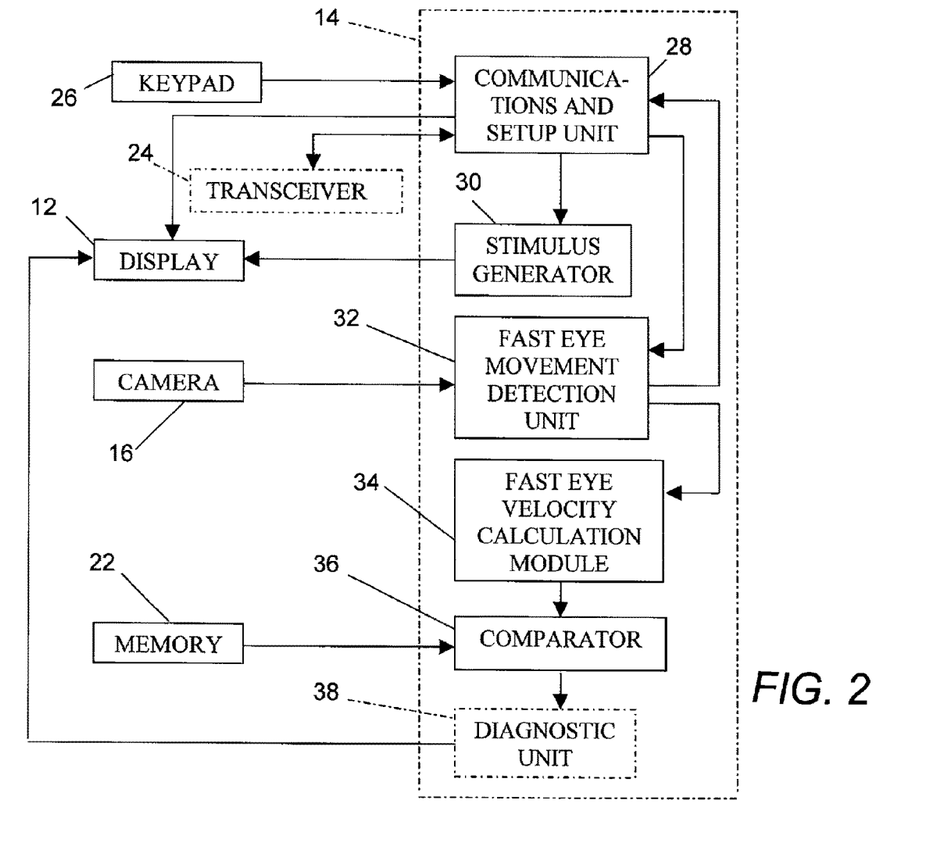
FIG. 2 is a block diagram depicting components of a computer or microprocessor shown in FIG. 1, as well as other elements shown in FIG. 1.

As illustrated in FIG. 2, computer or microprocessor 14 typically comprises a communications and setup unit 28 which is connected to keyboard 26 and to display 12 for interfacing with a user for purposes of calibration and the selection of operating parameters such as stimulus shape, size, and speed and direction of movement. To that end, communications and setup unit 28 is connected to a stimulus generator 30 which is in turn connected to display 12 for purposes of energizing selected pixels of the display to show a moving image.

Computer or microprocessor 14 also includes a fast eye velocity detection module 32 and a fast eye velocity calculation module 34. Detection module 34 is connected at an input to communications and setup unit 28 for receiving therefrom data pertaining to the characteristics of the stimulus, particularly the direction and speed of stimulus movement. Detection module 32 is also connected at an input to sensor device or camera 16 for receiving therefrom electrically encoded data pertaining to eye movement. Detection module 32 is connected to calculation module 34 and provides eye movement data thereto. Calculation module 34 computes a magnitude of fast eye movement depending on the data from detection module 32.

Computer or microprocessor 14 also incorporates a comparator 36 which is connected to calculation module 34 and memory 22 for comparing a contemporaneously calculated or determined velocity magnitude from calculation module 34 with a predetermined velocity threshold or magnitude from memory 22. The result of the comparison, indicative of normalcy or potential brain trauma, is communicated to the user via a diagnostics unit 38. Diagnostics unit 38 may provide the user with a qualitative indication such as "traumatic brain injury" or "light injury" or "normal." Alternatively, diagnostics unit 38 may provide the user with a numerical evaluation such as a percentage indicating a likelihood of brain injury. The diagnosis may be communicated to the user via display 12.

Keyboard 26 may be used to initiate a measurement process. Several measurements may be made automatically within the same diagnostic session. For instance, the stimulus may be induced to travel across the display 12 several times, with communications and setup unit 28 signaling the beginning and end of each stimulus transit.

Figure 3:
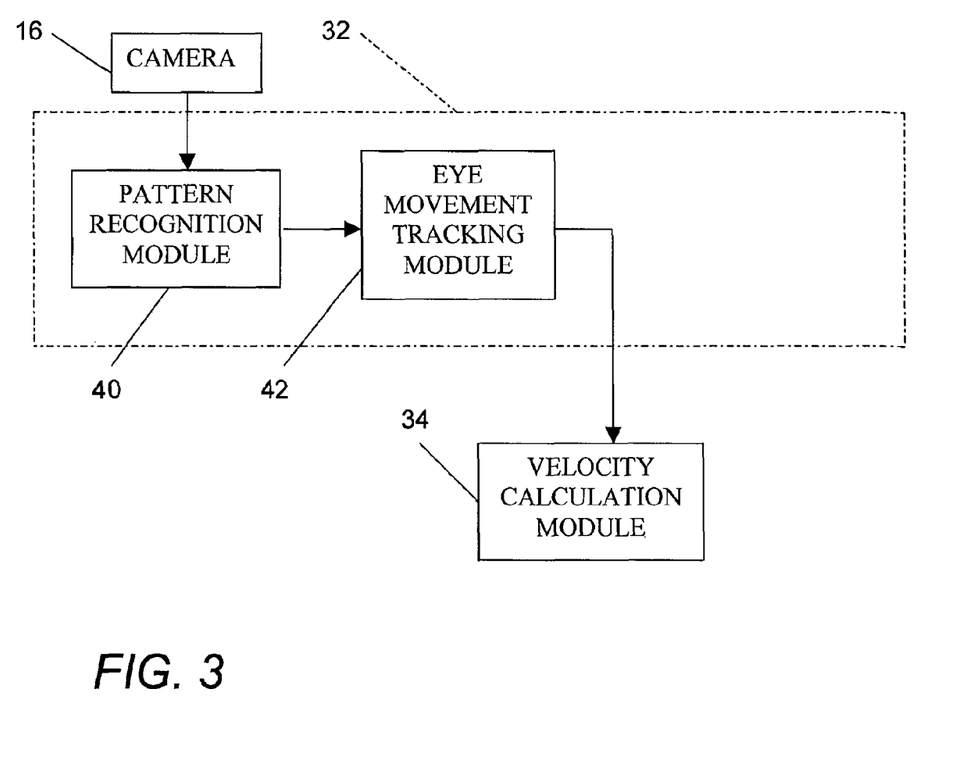
FIG. 3 is a block diagram depicting components of a fast eye movement detection unit shown in FIG. 2.

As illustrated in FIG. 3, detection module 32 may include a pattern recognition module 40 that identifies the fast eye velocity movement in part by analyzing an image of the subject to detect the orientation (angular position) of the subject's eye. Detection module 32 may additionally include an eye movement-tracking module 42 that compares successive eye orientations to detect a direction of movement of the eye and to generate a track or path of eye movement. Pattern recognition module 40 may further include a amplitude filter (not separately illustrated) that screens out eye movements of angular distances that are too long or too short to be fast eye movements. Concomitantly, velocity calculation module 34 may include a velocity filter (not separately illustrated) that screens out velocities that are too slow to be a fast eye velocity. Computer or microprocessor 14 naturally includes a time base or clock signal generator (not shown) that may be included in either detection module 32 or calculation module 34 or connected thereto, for enabling velocity calculations.

As indicated above, computer or microprocessor 14 is optionally connected to a transceiver 24 for transmitting eye movement data over a computer network and receiving a computed eye movement velocity or diagnostic result in return over the computer network. Alternatively or additionally, computer or microprocessor 14 may transmit the results of diagnostic testing over the computer network to a remote computer for reporting purposes.

Computer or microprocessor 14 may be configured for storing in memory 22 the results of testing for any particular subject. This enables comparison of contemporaneous fast eye velocity magnitudes with prior measurements for any given individual subject. Of course, where computer or microprocessor 14 transmits the eye velocity results to a remote computer, the remote computer and personnel having access thereto may perform the historical evaluations.

Prior to use of the above-described apparatus in monitoring a subject for potential undetected brain injury, there is an initial calibration process that allows computer or microprocessor 14 to determine/measure the amount of eye movement between fixed points of known distance between the points. The speed of eye movement is not a factor in this analysis. This calibration in turn permits subsequent calculations of the distance that the eye travels during testing which in turn, in the context of the time elapsed during the movement, permits calculation of the velocity of the eye movement.

What is being calibrated or quantified is the distance that the eye moves during the test. In order to identify this amount, before the test sequence, the amount of eye movement in millimeters is ascertained as the eye moves between a pair of fixed points placed so that the fixed points are separated by a desired distance (usually 20.degree. visual angle). With the knowledge of how much eye movement occurs, measured in millimeters, as the eye moves from one to another fixed point, that is to say across a known visual angle, one can subsequently deduce the amount of eye movement in degrees during the test.

It is to be noted that eye movement is detected by the actual amount of movement of landmarks on the eye. One approach is to capture an optical signal which is analyzed by computer to locate the iris-pupillary interface. This in turn permits detection of the center of the pupil circle, which is used as one point of reference, a point that moves with eye movement, for the calculation of eye position. One additional reference point on the eye is required to allow calculation of eye position. The optimal approach would have the second point not move regardless of eye movement. This is achievable by utilizing the first Purkinge image, the position of a reflected light pattern on the cornea. The light source to create this reflection can be infrared.

In a method for detecting minor traumatic brain injury, which may use the apparatus disclosed hereinabove, one presents to a subject a visual stimulus such as a bar, stripe, dot, icon, or graphic representation, or a series of bars, stripes, dots, icons, or graphic representations, which moves along a predetermined path across a visual field of the subject. Preferably, the stimulus is presented on a small electronic display 12 such as that of a handheld electronic device (notebook, cellphone, personal digital assistant) or on the lenses of glasses or goggles. In the latter case, the method further comprises removably attaching the casing 18 to a head of the subject prior to the presenting of the stimulus on display 12.

Eye movement of the subject is monitored while the subject views the stimulus. As indicated above, eye movement typically includes a slow eye velocity component, which responds to the predetermined movement of the stimulus, and an involuntary fast eye velocity component, which is particularly monitored for its rapidity. A user (who may also be the subject) operates the measurement apparatus 10 to determine a magnitude for the detected fast eye velocity component and to compare the determined magnitude with a predetermined numerical value to determine whether the subject has incurred minor traumatic brain injury.

Preferably, the monitoring of eye movement includes operating sensor device or camera 16, which is preferably, but not necessarily, mounted to the same casing 18 as display 12. The monitoring of eye movement preferably also includes operating digital computer of microprocessor 14, for instance, to carry out a pattern recognition process via pattern recognition module 40 and eye movement-tracking module 42 and to carry out a movement filtering process via fast eye velocity detection module 32 and fast eye velocity calculation module 34. Computer or processor 14 is also mounted to or housing in casing 18.

The magnitude for the detected fast eye velocity component may be determined by operating digital computer or microprocessor 14 and particularly calculation module 34 to carry out an arithmetic calculation. Where the selected parameter is eye movement velocity, the calculation is of distance divided by time—a velocity calculation. The distance may be an angular distance or a linear distance.

Calculation module 34 may be configured to carry out additional or alternative measures of the fast eye movement component. For example, calculation module 34 may be programmed to compile a table of eye movement amplitude as a function of eye velocity (or vice versa) and to compute an average and a measure of the degree of uniformity or deviation among the amplitudes or angular distances of the fast eye movements. Alternatively, calculation module 34 might compile a table of eye movement velocity as a function of amplitude or degree of eye movement and compute. If fast eye velocity falls below 2 standard deviations of norms for any degree of movement, that can be taken as an indicator of potential brain trauma.

It is to be noted that the various modules of computer or microprocessor 14 as shown in FIGS. 2 and 3 are realizable as generic digital processing circuits that are configured through software to perform the described functions. Alternatively, one or more of the various modules of FIGS. 1-3 may be implemented in the form of hard-wired circuits. This is particularly the case with transceiver 24, stimulus generator 30, and fast eye movement detection unit 32.

One may also operate computer or microprocessor 14 and particularly comparator 36 to ascertain whether the contemporaneously determined or calculated fast eye velocity magnitude bears such a relation to a predetermined numerical value as to be indicative of minor (otherwise undetectable) traumatic brain injury. Typically, if measured eye velocity falls below a predetermined threshold, then possible brain injury is to be assumed.

As indicated above, the determining of the eye velocity magnitude may be implemented at a remote station. In that event, eye movement data is transmitted over a computer network and a computed eye movement velocity is received in return over the computer network. The comparison of computed eye movement velocity with the predetermined numerical value may also be performed at a remote location by another computer. In that event, the result of the comparison may be transmitted back to the on site digital computer or microprocessor 14, either alone or together with a computed magnitude of the fast eye velocity component.

Preferably, however, both the determination of eye velocity magnitude and the comparison with predetermined numerical value or threshold are automatically performed through the operation of a programmed electronic device on site. This ensures that an evaluation may be made at any time and any place, regardless of access to a wireless or other network.

Although the present invention has been described with particularity herein, the scope of the present invention is not limited to the specific embodiment disclosed. It will be apparent to those of ordinary skill in the art that various modifications may be made to the present invention without departing from the spirit and scope thereof. The scope of the invention is not to be limited by the illustrative examples described above. The scope of the present invention is defined by the appended claims and equivalents thereto.

What is claimed is:

1. A method for detecting minor traumatic brain injury, comprising: presenting to a subject a visual stimulus having a predetermined direction and speed of movement across a visual field of the subject; monitoring movement of an eye of the subject while the subject views said stimulus, the eye movement including a slow eye velocity component responsive to said predetermined movement, the eye movement further including a fast eye velocity component, the monitoring of eye movement including detecting said fast eye velocity component; determining a magnitude of a parameter of the detected fast eye velocity component; and comparing the determined magnitude with a predetermined numerical value to determine whether the subject has incurred minor traumatic brain injury.

2. The method defined in claim 1 wherein the monitoring of eye movement includes operating a sensor device.

3. The method defined in claim 2 wherein said sensor device is a camera and a digital computer is operatively connected to said camera, the monitoring of eye movement including operating said digital computer to determine the magnitude of said parameter.

4. The method defined in claim 3 wherein said camera is taken from the group consisting of an optical camera and an infrared camera.

5. The method defined in claim 2 wherein the determining of said magnitude includes operating a computer or microprocessor to carry out an arithmetic calculation.

6. The method defined in claim 5 wherein said sensor device and said computer or microprocessor are housed in a casing, said casing being provided with a display, the presenting of said stimulus including operating said computer or microprocessor to provide said stimulus as a moving image on said display.

7. The method defined in claim 6, further comprising removably attaching said casing to a head of the subject prior to the presenting of said stimulus.

8. The method defined in claim 5 wherein the comparing of said determined magnitude with said predetermined numerical value includes operating said computer or microprocessor.

9. The method defined in claim 2 wherein the determining of said magnitude includes transmitting eye movement data over a computer network and receiving a computed eye movement velocity in return over said computer network.

10. The method defined in claim 1 wherein the determining of said magnitude and the comparing of the determined magnitude with said predetermined numerical value are automatically performed through the operation of a programmed electronic device.

11. The method defined in claim 1 wherein the parameter includes eye movement speed, the determining of said magnitude including measuring an amplitude or angular distance of eye movement during at least one instance of said fast eye velocity component and dividing said amplitude or angular distance by the time or duration of said one instance of said fast eye velocity component.

12. An apparatus for detecting minor traumatic brain injury, comprising: an image generator for presenting a visual stimulus having a predetermined movement across a visual field of a subject; a sensor device for monitoring movement of an eye of the subject while the subject views said stimulus, the eye movement including a slow eye velocity component responsive to said predetermined movement, the eye movement further including a fast eye velocity component, said sensor device being configured to generate a signal encoding detected positions of the subject's eye; and a computer or microprocessor operatively connected to said sensor device, said computer or microprocessor being configured for determining a magnitude of a parameter of the fast eye velocity component.

13. The apparatus defined in claim 12 wherein said computer or microprocessor is further configured for comparing said magnitude with a predetermined numerical value to determine whether the subject has incurred minor traumatic brain injury.

14. The apparatus defined in claim 12 wherein said sensor device is a camera taken from the group consisting of an optical camera and an infrared camera.

15. The apparatus defined in claim 12 wherein said sensor device and said computer or microprocessor are housed in a casing, said casing being provided with a display, said computer or microprocessor being operatively connected to said display for operating said display to provide said stimulus as a moving image on said display.

16. The apparatus defined in claim 15 wherein said casing has a hand-holdable configuration and size.

17. The apparatus defined in claim 15, further comprising a headband or cap for removably attaching said casing to a head of the subject.

18. The apparatus defined in claim 12 wherein said computer or microprocessor is further configured for transmitting eye movement data over a computer network and receiving a computed result in return over said computer network.

* * * * *